(12) United States Patent
Jung et al.

(10) Patent No.: US 11,130,941 B2
(45) Date of Patent: Sep. 28, 2021

(54) METHOD OF FABRICATING SUBSTRATE FOR CULTURING STEM CELL

(71) Applicant: RESEARCH & BUSINESS FOUNDATION SUNGKYUNKWAN UNIVERSITY, Suwon-si (KR)

(72) Inventors: Donggeun Jung, Seoul (KR); Sungyool Kwon, Suwon-si (KR); Wonjin Ban, Suwon-si (KR); Hyuna Lim, Suwon-si (KR); Yoonsoo Park, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 493 days.

(21) Appl. No.: 16/012,038

(22) Filed: Jun. 19, 2018

(65) Prior Publication Data
US 2018/0371419 A1   Dec. 27, 2018

(30) Foreign Application Priority Data
Jun. 22, 2017   (KR) .................. 10-2017-0079013

(51) Int. Cl.
| | |
|---|---|
| B05D 1/00 | (2006.01) |
| C12N 5/0775 | (2010.01) |
| C23C 16/50 | (2006.01) |
| B05D 3/04 | (2006.01) |
| C23C 16/30 | (2006.01) |

(Continued)

(52) U.S. Cl.
CPC ............. *C12N 5/0667* (2013.01); *B05D 1/62* (2013.01); *B05D 3/0486* (2013.01); *C23C 16/0245* (2013.01); *C23C 16/30* (2013.01); *C23C 16/4482* (2013.01); *C23C 16/50* (2013.01); *C23C 16/515* (2013.01); *B05D 3/141* (2013.01); *B05D 7/02* (2013.01); *B05D 7/24* (2013.01);

(Continued)

(58) Field of Classification Search
None
See application file for complete search history.

(56) References Cited

U.S. PATENT DOCUMENTS

| | | | |
|---|---|---|---|
| 8,962,097 B1 * | 2/2015 | Yokley ................... | B05D 3/144 427/535 |
| 2002/0034796 A1 * | 3/2002 | Shastri ................. | C12N 5/0068 435/173.1 |

(Continued)

FOREIGN PATENT DOCUMENTS

| | | | |
|---|---|---|---|
| JP | 62209140 A | * | 9/1987 |
| KR | 10-2009-0092689 A | | 9/2009 |

(Continued)

OTHER PUBLICATIONS

Guo et al. Enhanced adhesion/spreading and proliferation of mammalian cells on electropolymerized porphyrin film for biosensing applications. Biosensors and Bioelectronics. vol. 23 (2008) pp. 865-871. (Year: 2008).*

(Continued)

*Primary Examiner* — Cachet I Proctor
(74) *Attorney, Agent, or Firm* — NSIP Law

(57) ABSTRACT

The present disclosure relates to a method of fabricating a substrate for culturing stem cells, including forming a plasma polymer layer from a precursor material on a substrate using plasma, and the precursor material contains a heteroaromatic compound or a linear compound.

9 Claims, 9 Drawing Sheets

(51) Int. Cl.
*C23C 16/515* (2006.01)
*C23C 16/02* (2006.01)
*C23C 16/448* (2006.01)
*B05D 3/14* (2006.01)
*B05D 7/02* (2006.01)
*B05D 7/24* (2006.01)

(52) U.S. Cl.
CPC ...... B05D 2518/00 (2013.01); *C12N 2533/30* (2013.01)

(56) References Cited

U.S. PATENT DOCUMENTS

| | | | | |
|---|---|---|---|---|
| 2005/0287651 A1* | 12/2005 | Akimoto | ............... | C12P 7/6472 435/134 |
| 2009/0318609 A1* | 12/2009 | Badyal | .................... | B05D 1/62 524/548 |
| 2014/0295553 A1* | 10/2014 | Du | ......................... | C12M 23/10 435/377 |
| 2017/0158809 A1* | 6/2017 | Gleason | ................... | B05D 1/62 |
| 2018/0171299 A1* | 6/2018 | Cho | .................... | A61L 27/3895 |

FOREIGN PATENT DOCUMENTS

| | | | | |
|---|---|---|---|---|
| KR | 10-1132317 B1 | 4/2012 | | |
| WO | WO-2008147166 A1 * | 12/2008 | ............. | A61L 27/18 |

OTHER PUBLICATIONS

Cruz et al. Films obtained by plasma polymerization of pyrrole. Thin Solid Films. vol. 342 (1999) pp. 119-126 (Year: 1999).*
Pelto, Jani et al., "Novel Polypyrrole-Coated Polyactide Scaffolds Enhance Adipose Stem Cell Proliferation and Early Osteogenic Differentiation", *Tissue Engineering: Part A*, vol. 19, No. 7 and 8, 2013 (pp. 882-892).
Korean Office Action dated Sep. 14, 2018 in corresponding Korean Patent Application No. KR 10-2017-0079013 (5 pages in Korean).

* cited by examiner

METHOD OF FABRICATING SUBSTRATE FOR CULTURING STEM CELL

CROSS-REFERENCE TO RELATED APPLICATION

This application claims the benefit under 35 USC 119(a) of Korean Patent Application No. 10-2017-0079013 filed on Jun. 22, 2017, in the Korean Intellectual Property Office, the entire disclosure of which is incorporated herein by reference for all purposes.

TECHNICAL FIELD

The present disclosure relates to a method of fabricating a substrate for culturing stem cells, a substrate for culturing stem cells fabricated by the method, a method of culturing stem cells on the substrate for culturing stem cells, and a cell chip in which cells are fixed on the substrate for culturing stem cells.

BACKGROUND

As cell therapy using culture cells has been widely applied to the treatment for diseases, interest in cell culture is presently being increased. In general, cells are cultured in a cell culture container such as a culture dish, a culture flask, and a roller bottle which are artificially manufactured depending on characteristics of the culture cells in order to obtain a large number of cells.

Most of artificially cultured cells survive on the bottom of a cell culture container through growth, proliferation, and differentiation. However, some of the cells may form layers and proliferate on other cells and some of the cells may grow, proliferate and differentiate while being suspended in a cell culture medium.

However, a conventional cell culture container has different surface characteristics from an extracellular matrix on which cells reside, and, thus, the cell proliferation and differentiation efficiency may be decreased. Although various cells are being artificially proliferated and used for clinical treatment in practice, it is not easy to succeed in the induction of differentiation of various cells including stem cells for patient treatment.

In a conventional culture method for culturing stem cells, various culture devices including a cell culture dish are not manufactured in consideration of characteristics of stem cells. Therefore, the culture devices do not sufficiently reflect growth conditions of stem cells. Accordingly, stem cells have a long doubling time of 48 hours or more as compared with other cells.

Stem cells need to be unchanged in characteristics during culture, and the differentiation thereof needs to be inhibited except necessary differentiation. However, in the case where the conventional culture devices are used, there are limitations in regulating the growth of stem cells.

Accordingly, there has been a need for studies on culture devices manufactured in sufficient consideration of characteristics of stem cells, culture devices that facilitate easy differentiation into target cells, and a method of surface treatment for culture devices.

Korean Patent No. 10-1132317 relates to a method of manufacturing a substrate for fixing cells. The method of manufacturing a substrate for fixing cells disclosed in Korean Patent No. 10-1132317 includes coating a surface of the substrate with a precursor for the main purpose of fixing cells. However, Korean Patent No. 10-1132317 does not teach adhesion of stem cells, increase of growth efficiency, or maintenance of characteristics of stem cells.

Further, in recent years, studies on human life have made rapid progress starting with the Human Genome Project. As the studies on living things have progressed, the technology for rapidly analyzing and processing a lot of information about living things has emerged. Therefore, interest in biochips which can rapidly analyze information about living things has never been higher.

Biochips can be classified into DNA chips, protein chips, and cell chips depending on the kind of a biomaterial fixed to a substrate. At the initial stage of biochip development, the DNA chips were prominent in concert with understanding about human genetic information. However, as interest in proteins underlying life and cells which become the backbone of a living thing as a corporate body of proteins is increasing, the protein chips and the cell chips have currently received a lot of attention as biochips.

Particularly, the cell chips can fix a lot of cells without changing the properties thereof and thus are effective media that are accessible to a variety of fields such as the development of new medicines, genomics, proteomics and the like. When a cell is fixed to a substrate to grow and divide thereon, a cell analysis can be easily facilitated. For example, a cell chip makes it possible to easily observe how a cell reacts to a new medicine or another bodily material such as hormone.

However, there are several problems to overcome in developing such cell chips. First, cells are not fixed well on a substrate. Only when cells are fixed well on a substrate, the cells can grow and divide on the substrate. If cells cannot be fixed evenly on a substrate, there may be a problem in the growth and division of the cells. Further, being fixed well means that even a small number of cells can be fixed accurately. Since even a small number of cells can be fixed well on a substrate, the sensitivity of the substrate for the cell chip can be improved.

Second, when cells are fixed to a substrate, the properties of the cells need to be maintained. A cell chip may not function properly when cells, even if fixed well on a substrate, cannot grow well on the substrate and lose their inherent properties due to the properties of the substrate. Particularly, stem cells have various properties. Therefore, it is very important to maintain the properties of the cells. Accordingly, understanding of the above description is needed first when developing a cell chip.

The above information is presented as background information only to assist with an understanding of the present disclosure. No determination has been made, and no assertion is made, as to whether any of the above might be applicable as prior art with regard to the disclosure.

SUMMARY

In view of the foregoing, the present disclosure provides a method of fabricating a substrate for culturing stem cells.

Further, the present disclosure provides a substrate for culturing stem cells fabricated by the above-described fabrication method.

Furthermore, the present disclosure provides a method of culturing stem cells on the substrate for culturing stem cells fabricated by the above-described fabrication method.

Moreover, the present disclosure provides a cell chip in which cells are fixed on the substrate for culturing stem cells fabricated by the above-described fabrication method.

However, problems to be solved by the present disclosure are not limited to the above-described problems. There may be other problems to be solved by the present disclosure.

According to a first aspect of the present disclosure, there is provided a method of fabricating a substrate for culturing stem cells, including forming a plasma polymer layer from a precursor material on a substrate using plasma, and the precursor material contains a heteroaromatic compound or a straight-chain compound.

According to an embodiment of the present disclosure, the heteroaromatic compound may be represented by the following Chemical Formula 1, but may not be limited thereto.

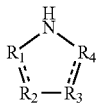

Chemical Formula 1

In Chemical Formula 1, $R_1$ to $R_4$ may be, each independently, represented by $\lfloor C-R_5 \rfloor$ or nitrogen and $R_5$ may represent, each independently, a hydrogen atom, an aldehyde group, a carboxyl group, a linear, branched chain or cyclic alkyl group or alkenyl group having 10 or less carbon atoms, or an aryl group having 12 or less carbon atoms.

According to an embodiment of the present disclosure, the heteroaromatic compound represented by Chemical Formula 1 may be any one heteroaromatic compound selected from the group consisting of pyrrole, pyrrolidine, pyrrole-2-carboxaldehyde, pyrrolidine-3-carboxylic acid, and combinations thereof, but may not be limited thereto.

According to an embodiment of the present disclosure, the heteroaromatic compound may include porphyrin, but may not be limited thereto.

According to an embodiment of the present disclosure, the straight-chain compound may be represented by the following Chemical Formula 2, but may not be limited thereto.

Chemical Formula 2

In Chemical Formula 2, $R_6$ may be a linear or branched saturated aliphatic radical having 1 to 24 carbon atoms and containing or not containing any one functional group selected from the group consisting of an amine group, an imine group, oxygen and combinations thereof.

According to an embodiment of the present disclosure, the straight-chain compound represented by Chemical Formula 2 may be any one straight-chain compound selected from the group consisting of ethylenediamine, diethylenetriamine, oxydiethanamine, and combinations thereof, but may not be limited thereto.

According to an embodiment of the present disclosure, the stem cells may be any one selected from the group consisting of neural stem cells, embryonic stem cells, induced pluripotent stem cells, mesenchymal stem cells, haematopoietic stem cells, and combinations thereof, but may not be limited thereto.

According to an embodiment of the present disclosure, the plasma polymer layer may be formed by chemical vapor deposition, but may not be limited thereto.

According to an embodiment of the present disclosure, the substrate may be formed of a material selected from the group consisting of glass, plastic, metal, and silicon, but may not be limited thereto.

According to an embodiment of the present disclosure, a surface of the substrate may be activated by performing a plasma process to any one gas selected from the group consisting of argon, hydrogen, nitrogen, helium, and combinations thereof, but may not be limited thereto.

According to an embodiment of the present disclosure, the gas may contain argon and hydrogen of from 20 sccm to 70 sccm and from 5 sccm to 20 sccm, respectively, but may not be limited thereto.

According to a second aspect of the present disclosure, there is provided a substrate for culturing stem cells fabricated by the method of fabricating a substrate for culturing stem cells.

According to a third aspect of the present disclosure, there is provided a method of culturing stem cells, including: fabricating a substrate for culturing stem cells by the method of fabricating a substrate for culturing stem cells; and culturing stem cells on the substrate for fixing the stem cells.

According to a fourth aspect of the present disclosure, there is provided a cell chip in which cells are fixed on a substrate for culturing stem cells fabricated by the method of fabricating a substrate for culturing stem cells.

The above-described embodiments are provided by way of illustration only and should not be construed as liming the present disclosure. Besides the above-described embodiments, there may be additional embodiments described in the accompanying drawings and the detailed description.

According to the above-described aspects of the present disclosure, it is possible to provide a method of fabricating a substrate for culturing stem cells, including forming a plasma polymer layer from a precursor material on a substrate using plasma.

A conventional cell culture container made of glass requires a pre-treatment process for coating adhesion molecules such as collagen, poly-D-lysine, fibronectin, etc. for cell adhesion. Further, a culture container made of plastic does not require the pre-treatment process and is disposable and thus does not require additional processes such as cleaning and sterilization processes. However, both the two culture containers take a long time to attach and grow cells and are not effective. For example, in a culture substrate fabricated using typical polystyrene being sold in the market, it is very difficult to culture cells. In order to use the culture substrate for culturing cells, a surface thereof needs to be modified through a special method. Any culture substrate for rapidly growing cells while maintaining the properties of stem cells has not yet been officially recognized.

A culture substrate fabricated by the method of fabricating a substrate for culturing stem cells in the present disclosure showed a remarkable improvement in stem cell culturing capability and adhesion as compared with a polystyrene substrate which is a control group and a culture substrate treated with hydrocarbon or argon/hydrogen plasma. In particular, it was confirmed that the culture substrate shows a cell culturing capability about two times higher than a conventional cell culture substrate known in the art and can culture cells with the highest density 96 hours after culture.

Therefore, the substrate for culturing stem cells according to the present disclosure can reduce the time required for culturing stem cells and also culture stem cells with a high density and thus can remarkably improve the cell culture efficiency.

Further, when stem cells are cultured on the substrate for culturing stem cells according to the present disclosure, even if cultured for a long period of time, the inherent properties of the stem cells can be maintained. Therefore, it is possible to provide a cell chip in which cells are fixed on the substrate for culturing stem cells.

The cell chip can be applied to the development of artificial organs, the development of chips for insertion into human body, the development of new medicines, genomics, and proteomics. Therefore, the substrate for culturing stem cells according to the present disclosure can be applied in various medical fields.

Other features and aspects will be apparent from the following detailed description, the drawings, and the claims.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
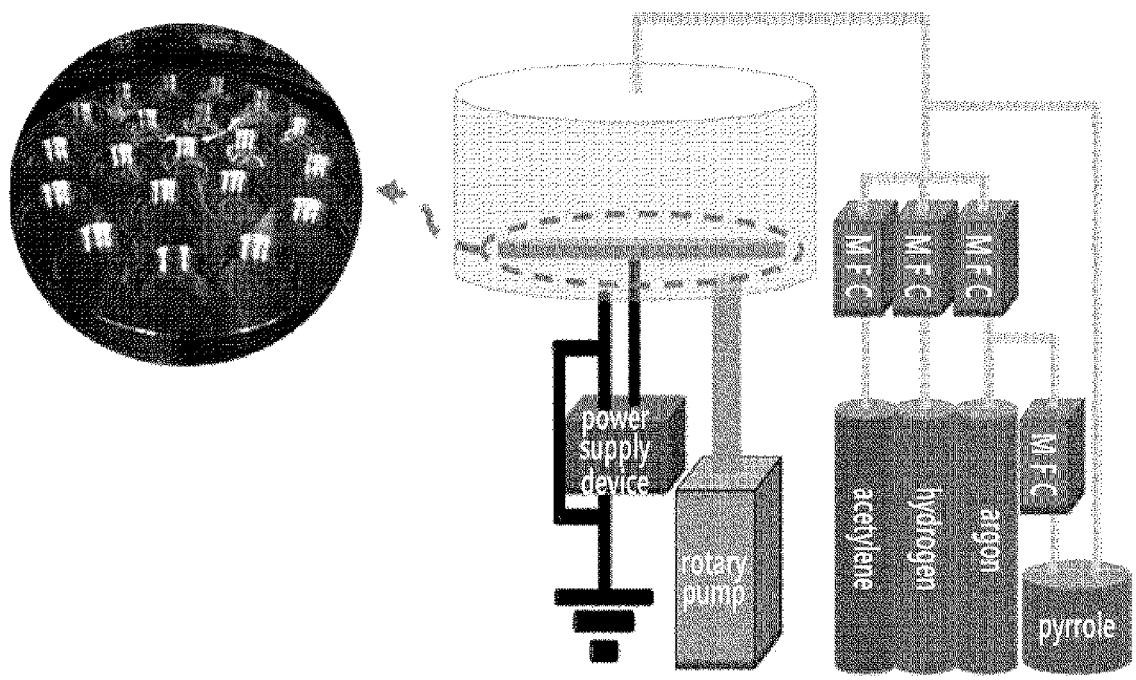
FIG. 1 is a schematic diagram illustrating a method of fabricating a substrate for culturing stem cells according to an embodiment of the present disclosure.

Hereinafter, embodiments of the present disclosure will be described in detail with reference to the accompanying drawings so that the present disclosure may be readily implemented by those skilled in the art.

However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the terms "on", "above", "on an upper end", "below", "under", and "on a lower end" that are used to designate a position of one element with respect to another element include both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereinafter, a method of fabricating a substrate for culturing stem cells, a substrate for culturing stem cells fabricated by the above-described fabrication method, a method of culturing stem cells on the substrate for culturing stem cells, and a cell chip in which cells are fixed on the substrate for culturing stem cells according to the present disclosure will be described in detail with reference to the following embodiments and examples and the accompanying drawings. However, the present disclosure may not be limited to the following embodiments, examples, and drawings.

A first aspect of the present disclosure relates to a method of fabricating a substrate for culturing stem cells, including forming a plasma polymer layer from a precursor material on a substrate using plasma, and the precursor material contains a heteroaromatic compound or a straight-chain compound.

According to an embodiment of the present disclosure, the heteroaromatic compound may be represented by the following Chemical Formula 1, but may not be limited thereto.

Chemical Formula 1

$$\begin{array}{c} \overset{H}{\underset{N}{\bigwedge}} \\ R_1 \diagup \diagdown R_4 \\ \underset{R_2}{\parallel} \underset{R_3}{\parallel} \end{array}$$

In Chemical Formula 1, $R_1$ to $R_4$ may be, each independently, represented by $^1C-R_{5\rfloor}$ or nitrogen and $R_5$ may represent, each independently, a hydrogen atom, an aldehyde group, a carboxyl group, a linear, branched chain or cyclic alkyl group or alkenyl group having 10 or less carbon atoms, or an aryl group having 12 or less carbon atoms.

According to an embodiment of the present disclosure, the heteroaromatic compound represented by Chemical Formula 1 may be any one heteroaromatic compound selected from the group consisting of pyrrole, pyrrolidine, pyrrole-2-carboxaldehyde, pyrrolidine-3-carboxylic acid, and combinations thereof, but may not be limited thereto.

According to an embodiment of the present disclosure, the heteroaromatic compound may include porphyrin, but may not be limited thereto.

According to an example of the present disclosure, a surface of a substrate was plasma-coated using, for example, pyrrole as a precursor, and then, adipose-derived stem cells (ADSCs) were cultured thereon. In this case, it was confirmed that cells about two times more than those of other control groups were cultured.

Further, according to another example of the present disclosure, the result of XPS analysis showed that the nitrogen content was the highest on a surface of a culture substrate coated with pyrrole and the cell culturing capability was also the highest on the surface of the culture substrate and thus confirmed that nitrogen of pyrrole has a positive effect on cell culture.

Furthermore, although ADSCs were cultured on the culture substrate coated with pyrrole according to the present disclosure for 96 hours, proteins CD44, CD73, or CD105 known as stem cell markers were expressed. Therefore, it was confirmed that the properties of the stem cells can be maintained even after a long period of culture.

According to an embodiment of the present disclosure, the straight-chain compound may be represented by the following Chemical Formula 2, but may not be limited thereto.

   Chemical Formula 2

In Chemical Formula 2, $R_6$ may be a linear or branched saturated aliphatic radical having 1 to 24 carbon atoms and containing or not containing any one functional group selected from the group consisting of an amine group, an imine group, oxygen and combinations thereof.

According to an embodiment of the present disclosure, the straight-chain compound represented by Chemical Formula 2 may be any one straight-chain compound selected from the group consisting of ethylenediamine, diethylenetriamine, oxydiethanamine, and combinations thereof, but may not be limited thereto.

A culture substrate coated with ethylenediamine having a linear structure including $NH_2$ also shows an excellent cell culturing capability. However, it could be seen that the culture substrate coated with pyrrole has a higher cell culturing capability than the culture substrate coated with ethylenediamine.

The forming of the plasma polymer layer with the precursor material means that the precursor material, a material derived from the precursor material and/or a material as a combination of materials derived from the precursor material and another material are integrated on an inner surface of the culture substrate using plasma to coat the surface.

According to an embodiment of the present disclosure, the stem cells may be any one selected from the group consisting of neural stem cells, embryonic stem cells, induced pluripotent stem cells, mesenchymal stem cells, haematopoietic stem cells, and combinations thereof, but may not be limited thereto.

The stem cells collectively refer to undifferentiated cells that have stemness properties and thus can differentiate into various types of cells. The stem cells differentiate into a specific cell by a specific differentiation factor and/or environment. Examples of the stem cells include embryonic stem cells, embryonic germ cells, adult stem cells, cancer stem cells, and the like. In recent years, studies for regenerating damaged tissue and treating various diseases such as diabetes, leukemia, Parkinson's disease, heart disease, spinal cord injury, etc. using stem cells which can differentiate into various cells have been actively conducted. Therefore, studies for differentiating stem cells into a specific cell are being attempted. Further, induced pluripotent stem cells (iPS) which are prepared from differentiated cells through a dedifferentiation process have been used for cell differentiation.

Mesenchymal stem cells and neural stem cells have been known as the adult stem cells. In particular, adipose-derived stem cells (ADSCs) as a kind of mesenchymal stem cells can be obtained from adipose tissue by enzyme digestion or the like and have been known as having potential for differentiation into various cells and tissue regeneration (Journal of Nippon Medical School Vol. 76 (2009) No. 2 P 56-66).

Accordingly, it is very important to develop a cell culture method capable of obtaining a large number of cells at a high density while maintaining the properties of stem cells or a substrate therefor.

According to an embodiment of the present disclosure, the plasma polymer layer may be formed by chemical vapor deposition, but may not be limited thereto.

The term "plasma" refers to a state in which electrically neutral gas molecules absorb electric energy or thermal energy to be divided into ions and electrons. Currently, studies on technologies using plasma are being actively conducted, and application fields thereof are being gradually expanded to plasma etching and plasma-enhanced chemical vapor deposition (PECVD) during a semiconductor process, surface treatment for metal or polymer, synthesis of new materials such as artificial diamond or the like, plasma display panel (PDP), and environment purification. In the case where plasma is used, a functional group can be uniformly integrated on a large-area substrate in a short time, which is suitable for mass production and thus advantageous for commercialization.

The plasma-enhanced chemical vapor deposition (PECVD) refers to a method of reacting a gaseous compound on a surface of a base material and depositing a product on the base material surface with the influence of plasma.

The PECVD has various advantages. First, it is possible to easily synthesize a material, which is difficult to synthesize due to its high melting point, at a temperature lower than the melting point. Second, the purity is high. Third, the PECVD is available for mass production, enables the deposition of various kinds of elements and compounds, and makes it easy to obtain thin films of various characteristics with good step coverage due to a wide range of process conditions.

According to an embodiment of the present disclosure, the substrate may be formed of a material selected from the group consisting of glass, plastic, metal, and silicon, but may not be limited thereto.

A conventional cell culture container made of glass requires a pre-treatment process for coating adhesion molecules such as collagen, poly-D-lysine, fibronectin, etc. for cell adhesion. Further, a culture container made of plastic does not require the pre-treatment process and is disposable and thus does not require additional processes such as cleaning and sterilization processes. However, both the two culture containers take a long time to attach and grow cells and are not effective.

In order to use the culture substrate for culturing cells, a surface thereof needs to be modified through a special method. Any culture substrate for rapidly growing cells while maintaining the properties of stem cells has not yet been officially recognized.

According to an embodiment of the present disclosure, a surface of the substrate may be activated by performing a plasma process to any one gas selected from the group consisting of argon, hydrogen, nitrogen, helium, and combinations thereof, but may not be limited thereto.

According to an embodiment of the present disclosure, the gas may contain argon and hydrogen of from 20 sccm to 70 sccm and from 5 sccm to 20 sccm, respectively, but may not be limited thereto.

Since the surface of the culture substrate is activated using a gas containing argon and hydrogen and coated with a precursor by plasma enhanced chemical vapor deposition, the cell adhesion can be improved.

A second aspect of the present disclosure provides a substrate for culturing stem cells fabricated by the method of fabricating a substrate for culturing stem cells.

The second aspect of the present disclosure relates to a substrate for culturing stem cells fabricated by the fabrication method according to the first aspect of the present disclosure. Detailed descriptions of the second aspect of the present disclosure, which overlap with those of the first aspect of the present disclosure, are omitted hereinafter, but the descriptions of the first aspect of the present disclosure may be identically applied to the second aspect of the present disclosure, even though they are omitted hereinafter.

A third aspect of the present disclosure provides a method of culturing stem cells, including: fabricating a substrate for culturing stem cells by the method of fabricating a substrate for culturing stem cells; and culturing stem cells on a substrate for fixing the stem cells.

According to an embodiment of the present disclosure, when stem cells are cultured on the substrate for culturing stem cells according to the present disclosure, even if cultured for a long period of time, the inherent properties of the stem cells can be maintained, and it is possible to reduce the time required for culturing stem cells and also culture stem cells with a high density and thus possible to remarkably improve the cell culture efficiency.

A third aspect of the present disclosure provides a method of culturing stem cells using a substrate for culturing stem cells fabricated by the fabrication method according to the first aspect of the present disclosure. Detailed descriptions of the third aspect of the present disclosure, which overlap with those of the first aspect of the present disclosure, are omitted hereinafter, but the descriptions of the first aspect of the present disclosure may be identically applied to the third aspect of the present disclosure, even though they are omitted hereinafter.

A third aspect of the present disclosure provides a method of culturing stem cells, including: fabricating a substrate for culturing stem cells by the method of fabricating a substrate for culturing stem cells; and culturing stem cells on a substrate for fixing the stem cells.

A fourth aspect of the present disclosure provides a cell chip in which cells are fixed on a substrate for culturing stem cells fabricated by the method of fabricating a substrate for culturing stem cells.

A fourth aspect of the present disclosure relates to a cell chip including a substrate for culturing stem cells fabricated by the fabrication method according to the first aspect of the present disclosure. Detailed descriptions of the fourth aspect of the present disclosure, which overlap with those of the first aspect of the present disclosure, are omitted hereinafter, but the descriptions of the first aspect of the present disclosure may be identically applied to the fourth aspect of the present disclosure, even though they are omitted hereinafter.

Hereinafter, the present disclosure will be explained in more detail with reference to Examples. However, the following Examples are illustrative only but do not limit the present disclosure.

EXAMPLE 1

Fabrication of Substrate for Culturing Stem Cells

A substrate for culturing stem cells of the present disclosure was fabricated using a polystyrene petri dish (Product of SPL: SPL10090 (bare polystyrene), Inner diameter: 85 mm, Outer height: 20.00 mm, Internal culture area: 57.50 $cm^2$).

Plasma-enhanced chemical vapor deposition (PECVD) was used for inner surface treatment of the polystyrene culture substrate (900 V, 0.5 A, 50 kHz, +100 V, Pulsed DC), and hydrogen ($H_2$, 99.999%) and argon (Ar, 99.999%) gases were used. As shown in FIG. 1, hydrogen and argon gases were mixed at a ratio of 50 sccm and 10 sccm using a mass flow controller (MFC) and then injected into a chamber and allowed to flow onto an inner surface of the culture substrate through a shower head. Then, an $Ar/H_2$ plasma process was performed to the inner surface of the culture substrate at 900 V for 10 minutes. During the $Ar/H_2$ plasma process, a processing pressure in the chamber was maintained at 30 mTorr. Through the plasma process using hydrogen and argon, the surface of the culture substrate was activated and cleaned. After the surface treatment with $Ar/H_2$ for improvement in adhesion of a thin film during a subsequent process, a pyrrole plasma polymerized thin film was deposited. In order to deposit the pyrrole plasma polymerized thin film, a pyrrole precursor was used in a bubbler. An argon gas was injected into the bubbler with the pyrrole to evaporate the pyrrole, and the evaporated pyrrole was injected into the chamber. In this case, the argon gas of 20 sccm was injected into the bubbler using the MFC. The processing pressure in the chamber was maintained at 30 mTorr. In order to check cell adhesion and culturing capability and a change in chemical composition on a surface depending on plasma discharge power, thin films were deposited under the conditions (100 V, 300 V, 600 V 900 V), 0.5 A, 50 kHz, +100 V, Pulsed DC) as shown in the following Table 1, and each deposition process was performed for 5 minutes.

TABLE 1

| Sample | Gas flow (sccm) | | Power (V) | |
|---|---|---|---|---|
| | Argon | Pyrrole | | |
| Control PS | — | — | — | |
| Pyrrole_1 | 80 | 20 | 100 V | Argon/hydrogen process-5 minutes |
| Pyrrole_2 | 80 | 20 | 300 V | Argon/hydrogen process-5 minutes |
| Pyrrole_3 | 80 | 20 | 600 V | Argon/hydrogen process-5 minutes |
| Pyrrole_4 | 80 | 20 | 900 V | Argon/hydrogen process-5 minutes |

COMPARATIVE EXAMPLE 1

As a control group, a surface-treated polystyrene culture dish manufactured by SPL (Products of SPL: SPL20100) was used.

TEST EXAMPLE 1

Adipose-derived stem cells (ADSCs) were cultured on the culture substrate fabricated in Example 1 to check cell adhesion and culturing capability and a change in chemical composition on a surface depending on plasma discharge power. Further, the culture substrate fabricated in Example 1 was compared in cell growth rate with the cell culture substrate manufactured by SPL. The ADSCs were cultured in a 37° C., 5% $CO_2$ incubator using a Dulbecco's Modified Eagle's Medium (DMEM) (Wel GENE Inc.) containing 10% fetal bovine serum (Wel Gene Inc.) and antibiotics (penicillin/streptomycin, Wel GENE Inc.). The ADSCs were separated from the substrate surface using a TE buffer solution (0.05% porcine trypsin), 0.5M ethylene diamine tetraacetic acid (EDTA), and phenol red contained in phosphate-buffer saline (PBS) and equally distributed to the culture substrates fabricated under the respective conditions and cultured in the 37° C., 5% $CO_2$ incubator using the DMEM. Then, the cells were examined under an optical microscope. After 96 hours, the number of cells was counted using a hemocytometer and the average value was used for the evaluation of cell adhesion.

Figure 2:
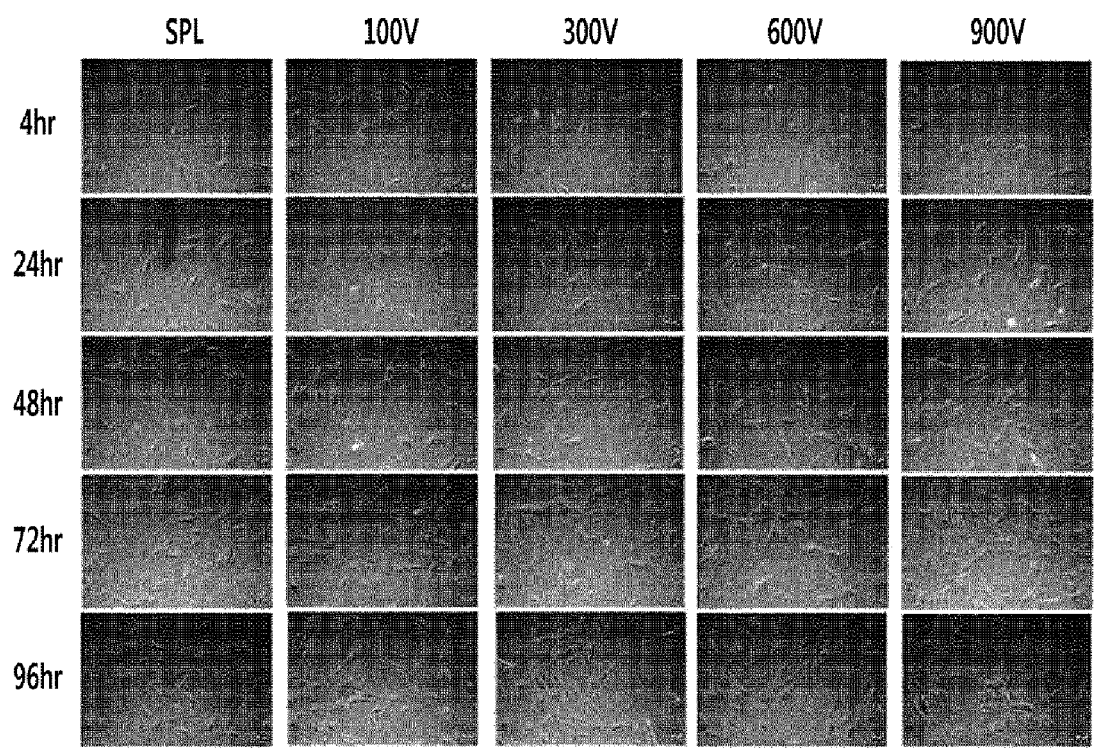
FIG. 2 provides images showing the effects of discharge power on the adhesion of adipose-derived stem cells (AD-SCs) during a plasma process when a culture substrate is fabricated according to an embodiment of the present disclosure.

As a result, it could be seen from FIG. 2 that the ADSCs were grown better on the culture substrates treated with plasma at 100 V, 300 V, 600 V, or 900 V than on the cell culture substrate manufactured by SPL.

Figure 3A:
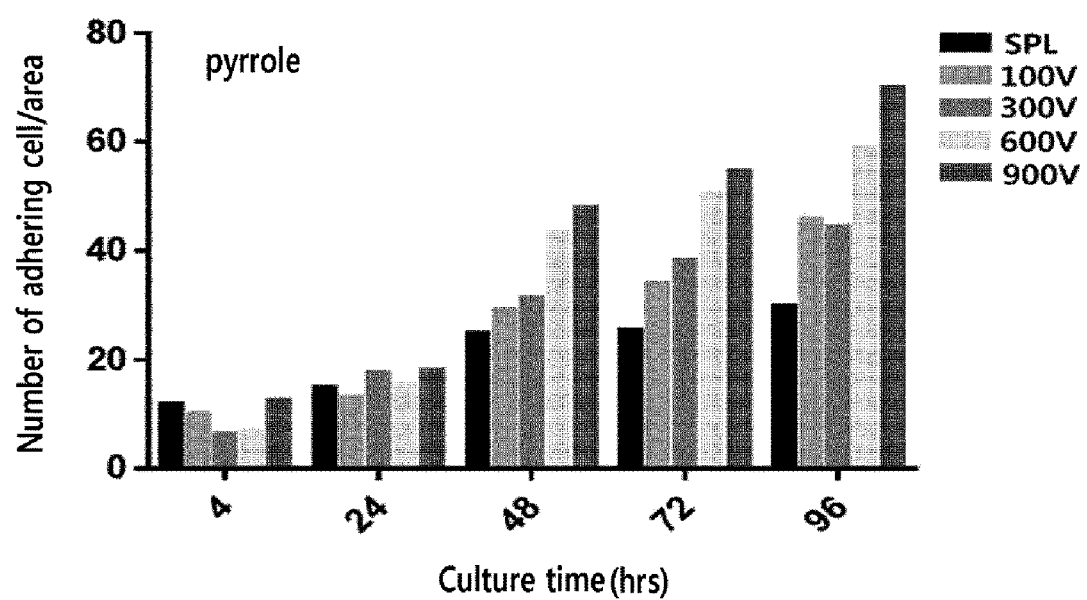
FIG. 3A shows the result of checking the number of ADSCs adhering to a culture substrate whose surface is coated with pyrrole according to an example of the present disclosure.
Figure 3B:
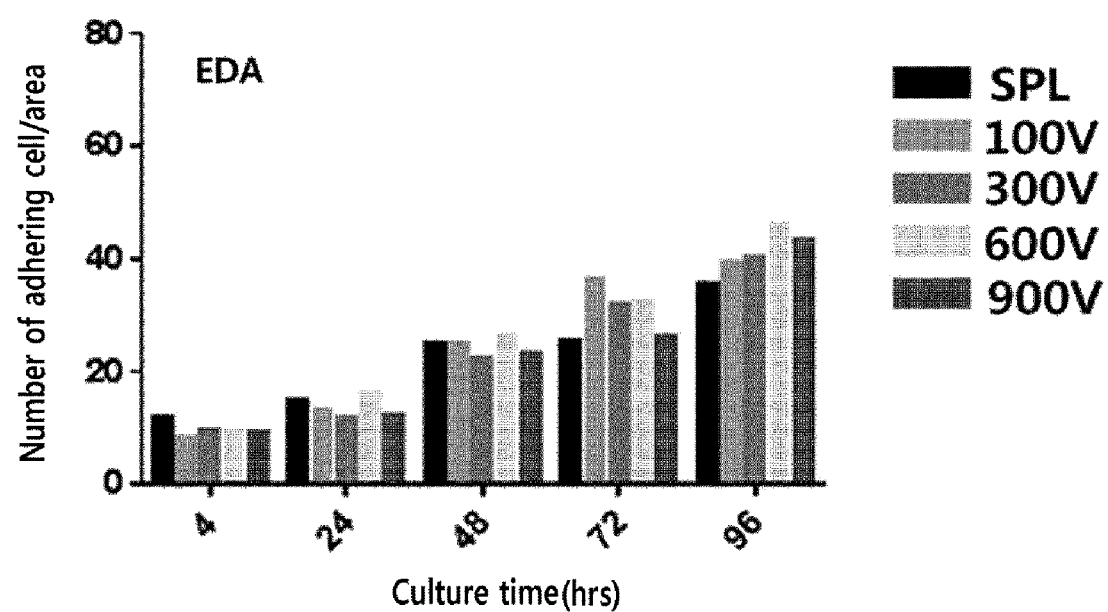
FIG. 3B shows the result of checking the number of ADSCs adhering to a culture substrate whose surface is coated with ethylenediamine (EDA).

Further, culture substrates coated with pyrrole and a culture substrate coated with EDA were compared in cell growth rate, and a result thereof was as shown in FIG. 3A and FIG. 3B. After the ADSCs were cultured on the control culture dish manufactured by SPL and the culture substrates fabricated with plasma power of 100 V, 300 V, 600 V or 900 V and coated with pyrrole, cell adhesion of each substrate was compared as shown in FIG. 3A. As a result, as the plasma power increased, the number of cells adhering to a predetermined area increased. The number of cells cultured on the culture substrate fabricated with 900 V was the highest at 74, and the cell adhesion of the culture substrate fabricated with 900 V was improved about 2 times compared with the control culture substrate manufactured by SPL.

Further, after the ADSCs were cultured on the control culture dish manufactured by SPL and the culture substrates fabricated with plasma power of 100 V, 300 V, 600 V or 900 V and coated with EDA, cell adhesion of each substrate was compared as shown in FIG. 3B. As a result, the number of cells cultured on the culture substrate fabricated with 900 V was the highest at 45, and the cell adhesion of the culture substrate fabricated with 900 V was improved about 1.2 times compared with the culture substrate manufactured by SPL.

Therefore, it was confirmed that pyrrole is more suitable for ADSC culture according to the test result under the same conditions. That is, it could be seen that the growth rate of the ADSCs on a culture substrate coated with pyrrole is much higher than on a culture substrate coated with EDA. Furthermore, it was confirmed that the ADSCs were grown on the pyrrole-coated culture substrate with the highest density 96 hours after culture.

TEST EXAMPLE 2

Also, the chemical composition on a surface of a culture substrate coated with pyrrole of the present disclosure was checked through X-ray photoelectron spectroscopy (XPS).

The XPS was performed using an ESCALAB250 (VG Microtech, UK) and also using monochromatic Al—Kα x-ray source (1486.6 eV). The spectra were calibrated to the Carbon 1s electron peak at 248.6 eV. High resolution spectra were generated by Shirley background subtraction, and deconvoluted using mixed Gaussian-Lorentzian functions.

Figure 4:
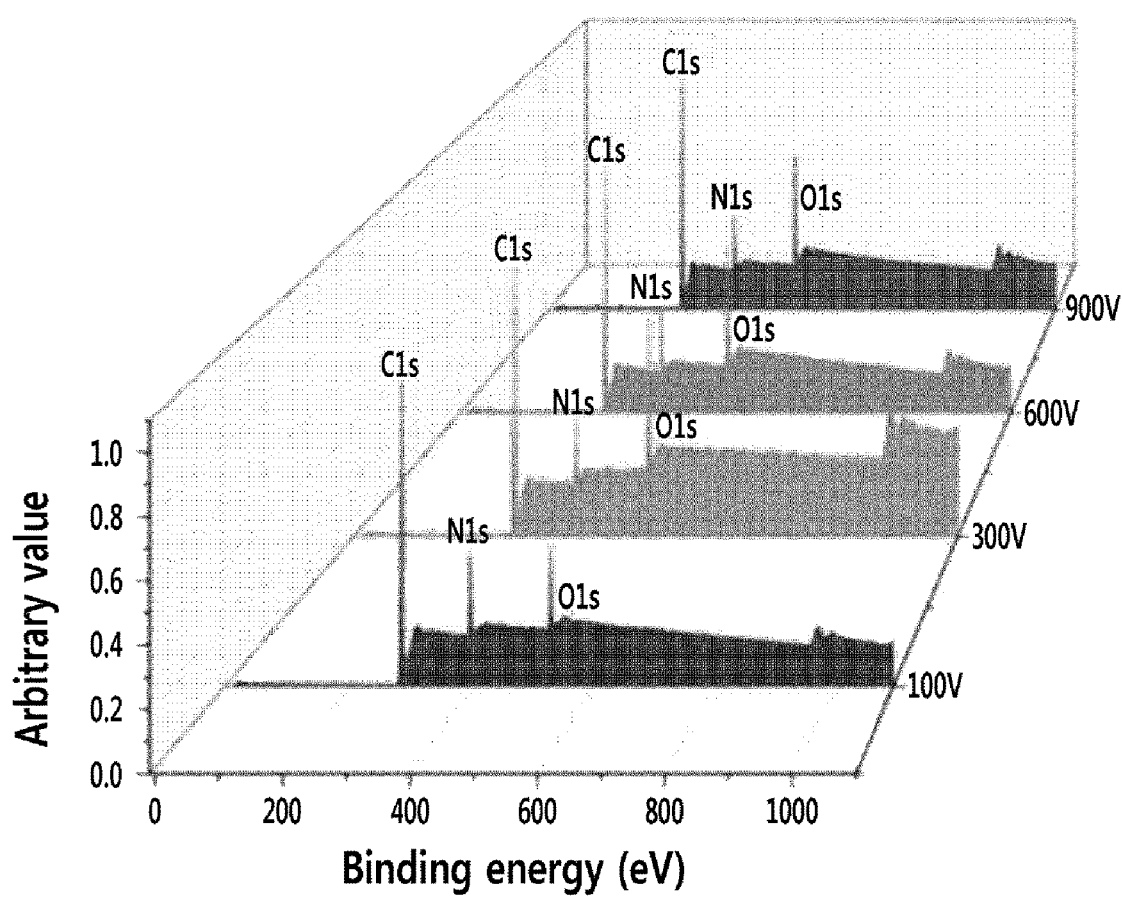
FIG. 4 shows the result of X-ray photoelectron spectroscopy (XPS) analysis of a culture substrate whose surface is coated using pyrrole as a precursor according to an example of the present disclosure.

The result thereof was as shown in FIG. 4, FIG. 5, and the following Table 2.

TABLE 2

| Sample | Atomic percentage (%) | | | Peak area ratio (%) C1s | | | Peak area ratio (%) N1s | | |
|---|---|---|---|---|---|---|---|---|---|
| | C | N | O | C—C C—H | C—O (C—N) | C=O (C=N) | N=C | $NH_2$ | N—C=O |
| Control PS | 98.7 | 0.5 | 0.8 | 98.34 | | 1.66 | | | |
| Pyrrole_1 (100 V) | 79.96 | 11.14 | 8.9 | 67.98 | 24.83 | 7.19 | 83.30 | 3.19 | 12.72 |
| Pyrrole_2 (300 V) | 73.1 | 10.78 | 16.02 | 68.48 | 20.32 | 11.20 | 54.59 | 25.52 | 19.88 |
| Pyrrole_3 (600 V) | 75.2 | 10.85 | 13.96 | 65.55 | 24.61 | 9.85 | 73.95 | 10.63 | 15.42 |
| Pyrrole_4 (900 V) | 73.17 | 12.31 | 14.52 | 69.29 | 11.36 | 19.52 | 52.75 | 21.10 | 26.15 |

FIG. 4 shows the atomic percentage on the surface through XPS wide scan spectra. It can be seen that as the plasma increases from 100 V to 900 V, the nitrogen concentration on the surface of the culture substrate increases. Also, it can be seen that carbon and oxygen are present on the surface.

Figure 5A:
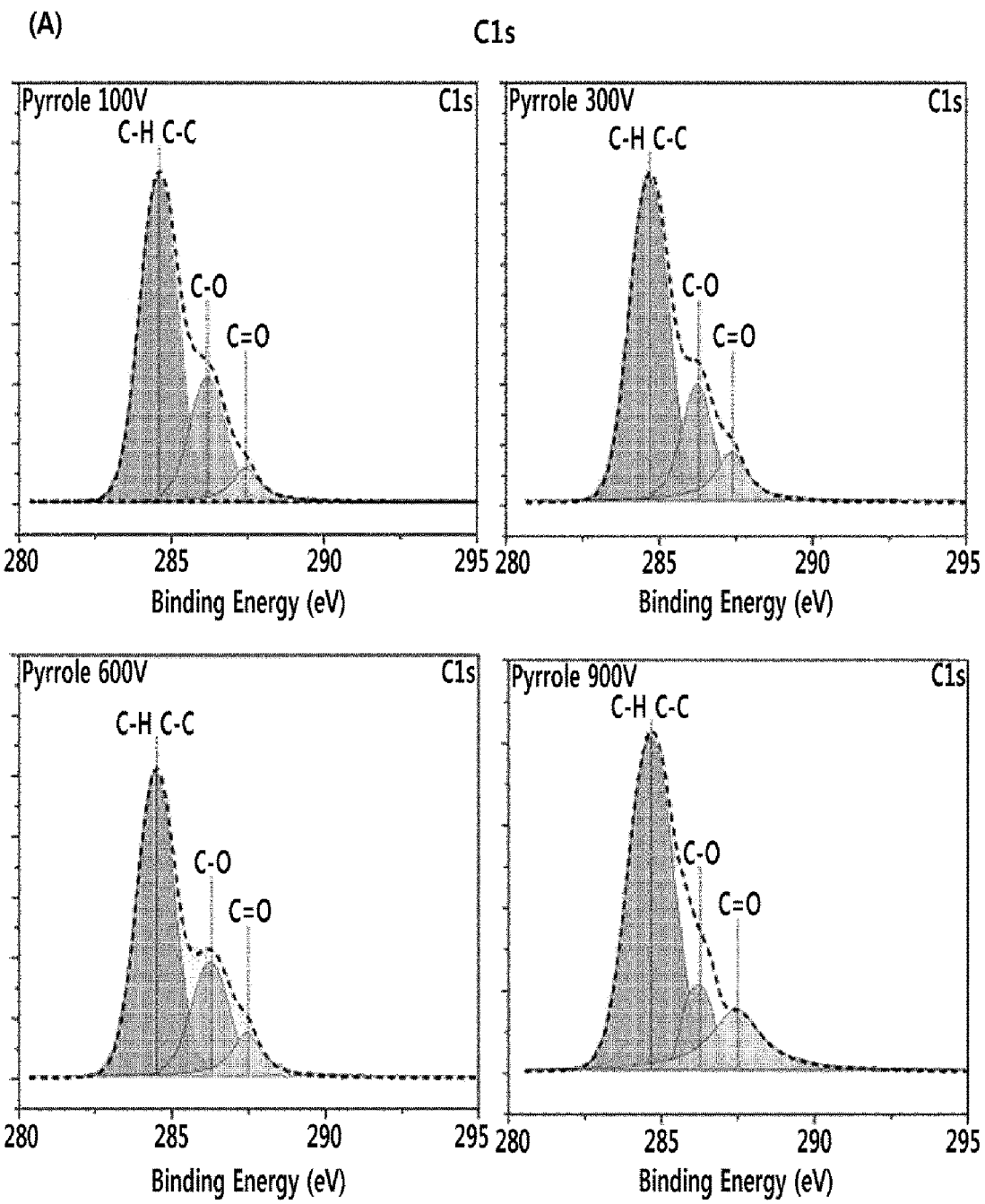
FIG. 5A shows XPS C1s peaks of a chemical functional group on a surface of a culture substrate according to an example of the present disclosure.

FIG. 5A shows the result of checking chemical functional groups present on the surface by fitting XPS C1s around 284.6 (C—H), 286.2 (C—O), and 287 (C=O) eV.

Figure 5B:
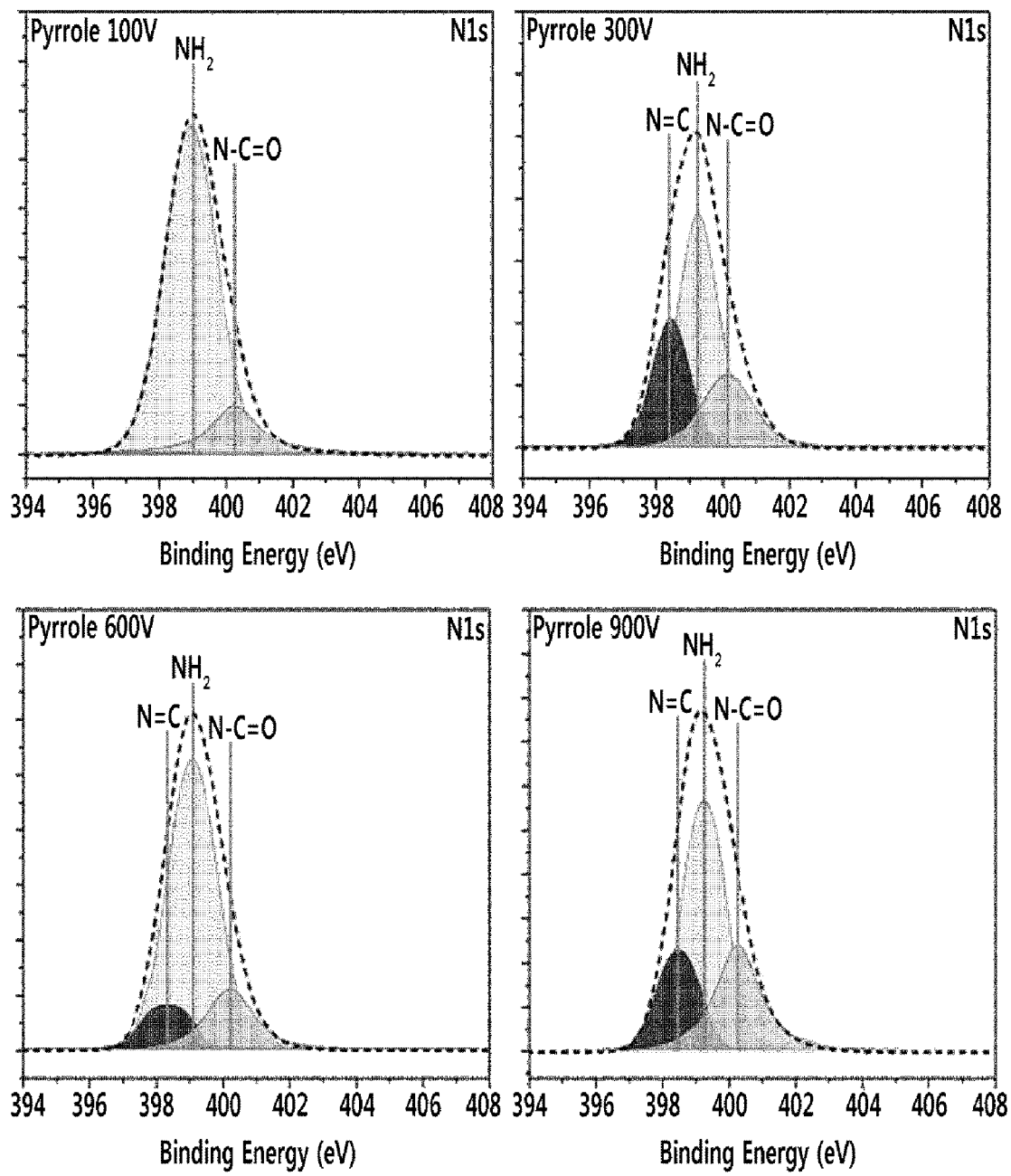
FIG. 5B shows XPS N1s peaks of a chemical functional group on a surface of a culture substrate.

FIG. 5B shows the result of checking chemical functional groups present on the surface by fitting XPS C1s around 400.2 (N=C), 401.2 ($NH_2$), and 402 (N—C=O) eV. It was confirmed that most $NH_2$ functional groups were present on the culture substrate fabricated with 900 V.

TEST EXAMPLE 3

Then, the correlation between a nitrogen/carbon atomic percentage ratio on the surface of the pyrrole-coated culture substrate of the present disclosure and the cell adhesion were checked.

Figure 6:
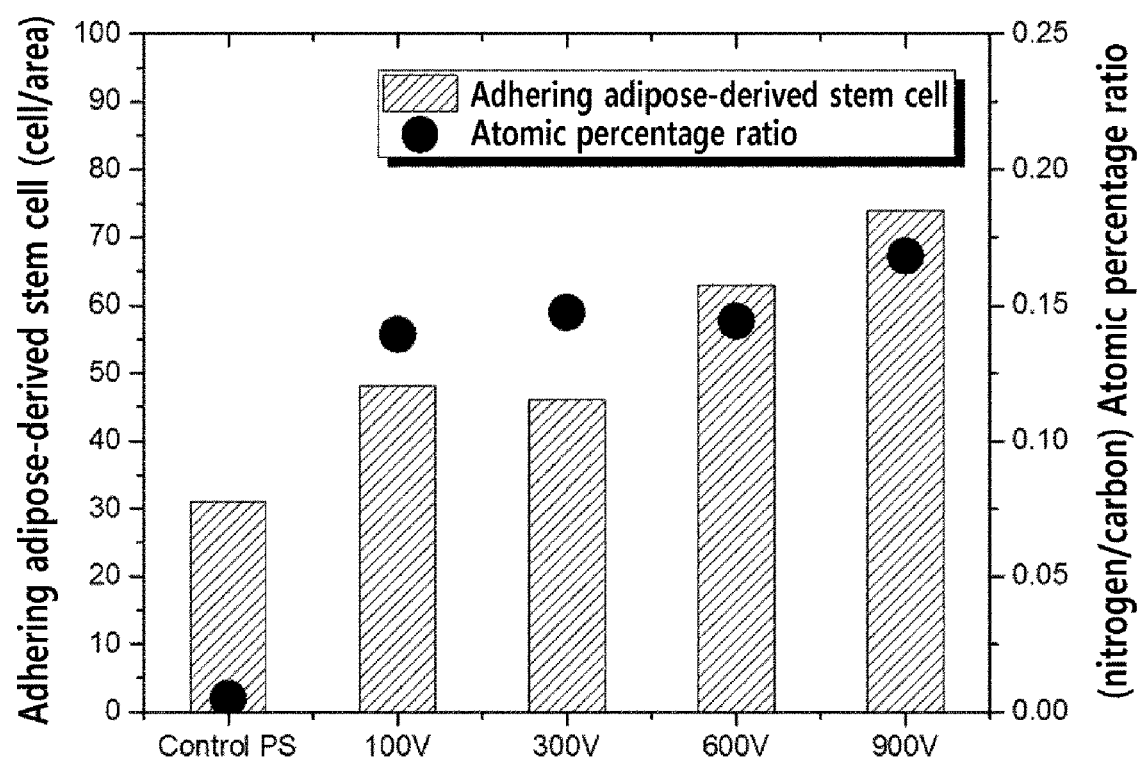
FIG. 6 shows the result of checking the correlation between a nitrogen concentration on a surface of a culture substrate and the cell adhesion according to an example of the present disclosure.

As a result, all the samples showed a higher nitrogen/carbon atomic percentage ratio than the control and the sample treated with plasma at 900 V showed the highest nitrogen/carbon atomic percentage ratio as shown in FIG. 6. Further, all the samples showed a higher cell adhesion than the control.

TEST EXAMPLE 4

After ADSCs were cultured for 96 hours on the culture substrate coated with pyrrole according to the present disclosure, whether or not the properties of stem cells can be maintained was checked.

To this end, the ADSCs were cultured as described in Test Example 1 and the expression of CD44, CD73 and CD105 known as stem cell markers was checked through Western Blot.

First, protein (20 μg) in a water-soluble lysate was analyzed using SDS-PAGE (polyacrylamide gel electrophoresis) and transferred to PVDF (polyvinylidene difluoride, Millipore, USA). The PVDF refers to a solution in which 0.5% non-fat milk is contained in Phosphate-buffered saline including 0.1% Tween-20, pH7.4 (PBST) and was blocked for 1 hour at room temperature. Then, the PVDF was allowed to react with an antibody specific to CD44 (Cell signaling), CD73 (Abcam), CD105 (Abcam) and actin (Santa Cruz) to examine the expression of protein. The PVDF allowed to react with the antibody was completely washed with PBST and cultured at room temperature for 1 hour with a secondary antibody combined with horseradish peroxidase (HRP). After secondary culture, the PVDF was checked using an enhanced chemiluminescence detection method (Amersham, USA).

Figure 7:
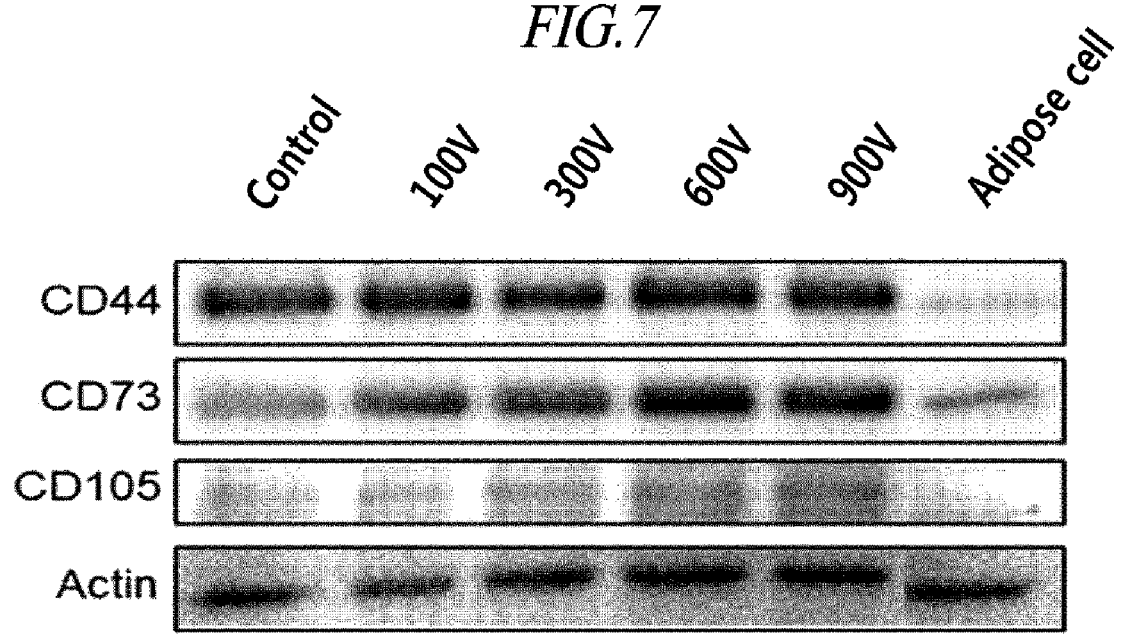
FIG. 7 shows the result of checking the properties of stem cells after culturing the stem cells on a culture substrate for 96 hours according to an example of the present disclosure.

As a result, it could be seen from FIG. 7 that CD44, CD73, and CD 105 which are stem cell markers were expressed, and, thus, the properties of the ADSCs were maintained despite 96 hours of culture.

The above description of the present disclosure is provided for the purpose of illustration, and it would be understood by those skilled in the art that various changes and modifications may be made without changing technical conception and essential features of the present disclosure.

Thus, it is clear that the above-described embodiments are illustrative in all aspects and do not limit the present disclosure. For example, each component described to be of a single type can be implemented in a distributed manner. Likewise, components described to be distributed can be implemented in a combined manner. The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:
1. A method of fabricating a substrate for culturing stem cells, comprising:
forming a plasma polymer layer from a precursor material on a substrate using plasma,
wherein the precursor material contains a heteroaromatic compound, and
wherein the heteroaromatic compound contains nitrogen and is represented by the following Chemical Formula 1, and
wherein a nitrogen content at the surface of the plasma polymer layer is increased by adjusting a voltage of the plasma:

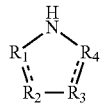

Chemical Formula 1 wherein in Chemical Formula 1, $R_1$ to $R_4$ are, each independently, represented by $^|C-R_5_|$ or nitrogen and $R_5$ represents, each independently, a hydrogen atom, an aldehyde group, a carboxyl group, a linear, branched chain or cyclic alkyl group or alkenyl group having 10 or less carbon atoms, or an aryl group having 12 or less carbon atoms.

2. The method of fabricating a substrate for culturing stem cells of claim 1,
wherein the heteroaromatic compound represented by Chemical Formula 1 is any one heteroaromatic compound selected from the group consisting of pyrrole, pyrrolidine, pyrrole-2-carboxaldehyde, pyrrolidone-3-carboxylic acid, and combinations thereof.

3. The method of fabricating a substrate for culturing stem cells of claim 1,
wherein the stem cells are any one selected from the group consisting of neural stem cells, embryonic stem cells, induced pluripotent stem cells, mesenchymal stem cells, haematopoietic stem cells, and combinations thereof.

4. The method of fabricating a substrate for culturing stem cells of claim 1,
wherein the plasma polymer layer is formed by chemical vapor deposition.

5. The method of fabricating a substrate for culturing stem cells of claim 1,
wherein the substrate is formed of a material selected from the group consisting of glass, plastic, metal, and silicon.

6. The method of fabricating a substrate for culturing stem cells of claim 1,
wherein a surface of the substrate is activated by performing a plasma process to any one gas selected from the group consisting of argon, hydrogen, nitrogen, helium, and combinations thereof.

7. The method of fabricating a substrate for culturing stem cells of claim 6,
wherein the gas contains argon and hydrogen of from 20 sccm to 70 sccm and from 5 sccm to 20 sccm, respectively.

8. The method of fabricating a substrate for culturing stem cells of claim 1,
wherein a nitrogen/carbon atomic percentage ratio at the surface of the plasma polymer layer is increased by adjusting a voltage of the plasma.

9. A method of fabricating a substrate for culturing stem cells, comprising:
forming a plasma polymer layer from a precursor material on a substrate using plasma,
wherein the precursor material contains a heteroaromatic compound, and
wherein the heteroaromatic compound comprises porphyrin.

* * * * *